United States Patent [19]
Gregory

[11] 3,967,645
[45] July 6, 1976

[54] CHECK VALVE FOR URINE COLLECTION DEVICE

[75] Inventor: Roy Gregory, Sierra Madre, Calif.

[73] Assignee: Urocare Products, Inc., El Monte, Calif.

[22] Filed: Jan. 3, 1975

[21] Appl. No.: 538,460

Related U.S. Application Data

[63] Continuation-in-part of Ser. No. 436,442, Jan. 25, 1974, abandoned.

[52] U.S. Cl. ............................................. 137/525.1
[51] Int. Cl.² ....................................... F16K 15/14
[58] Field of Search ............ 137/525.1, 525.3, 525.5

[56] References Cited
UNITED STATES PATENTS

| | | | |
|---|---|---|---|
| 175,145 | 3/1876 | Painter | 137/525.1 |
| 657,007 | 8/1900 | Richter | 137/525.1 X |
| 2,352,642 | 7/1944 | Langdon | 137/525.1 |
| 2,446,571 | 8/1948 | Browne | 137/525.1 |
| 2,662,724 | 12/1953 | Kravagna | 137/525.1 |
| 3,387,624 | 6/1968 | Soucy | 137/525.1 |
| 3,463,159 | 8/1969 | Heimlich | 137/525.1 X |
| 3,504,699 | 4/1970 | Grise | 137/525.1 |
| 3,566,964 | 3/1971 | Livingston | 137/525.1 X |
| 3,789,871 | 2/1974 | Tupper | 137/525.1 X |

Primary Examiner—William R. Cline
Attorney, Agent, or Firm—Christie, Parker & Hale

[57] ABSTRACT

A check valve between a catheter and a urine collection bag for an incontinent person must pass urine in the forward direction without significant head and must be free of back leakage to prevent infection. This valve has a rigid body so that the elastomeric sealing member mounted therein is not disturbed by the wearer's clothing. The sealing member has a pair of flat, parallel, normally spaced apart, sealing leaves integrally joined together along their lateral edges by webs to define a flat tube having a flat normally open passage therethrough. Means are provided for pressing on the lateral edges of the leaves for forcing the edges of the passage closed. The leaves are thin, soft elastomer, and the side edges are free to deflect laterally so that urine will pass forwardly through the valve in dropwise fashion, and the valve can also handle appreciable flow rates. Back pressure on the valve urges it closed. Preferably the means holding the valves leaves together are clips free from the rigid body.

14 Claims, 10 Drawing Figures

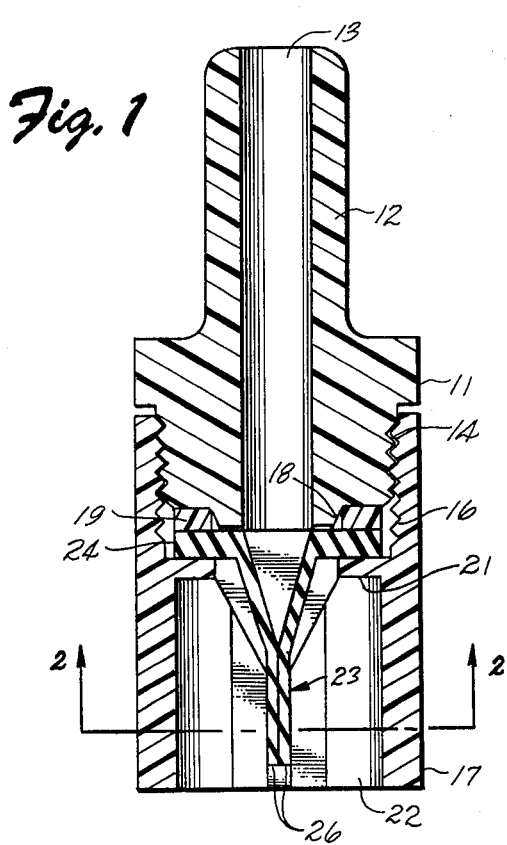
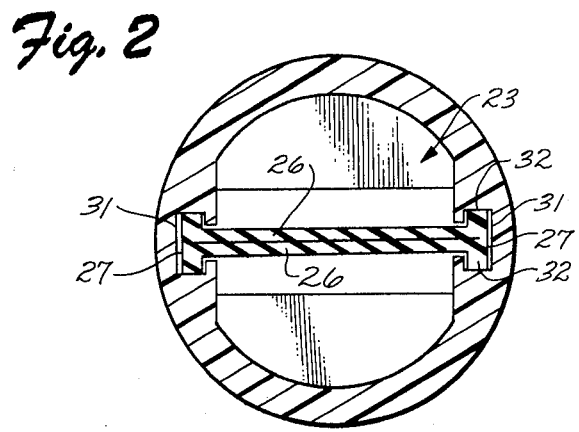
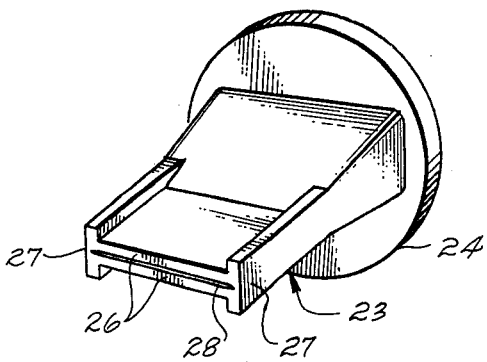
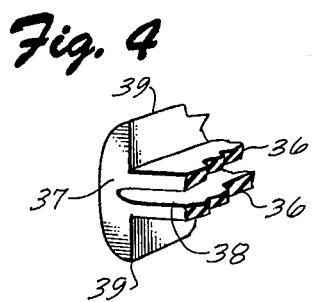
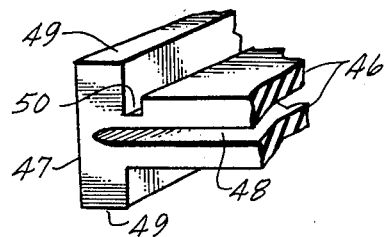
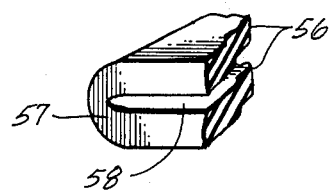
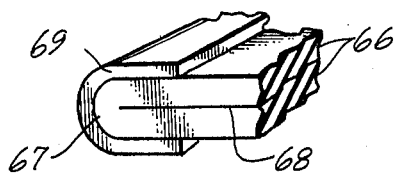

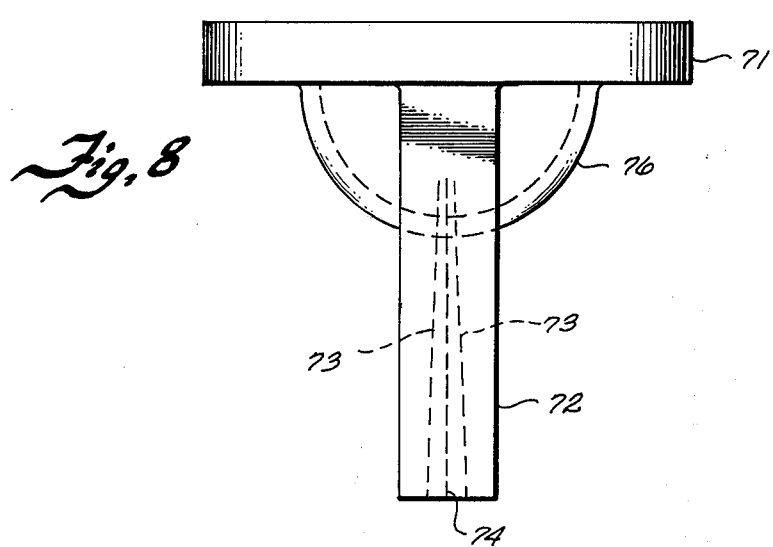
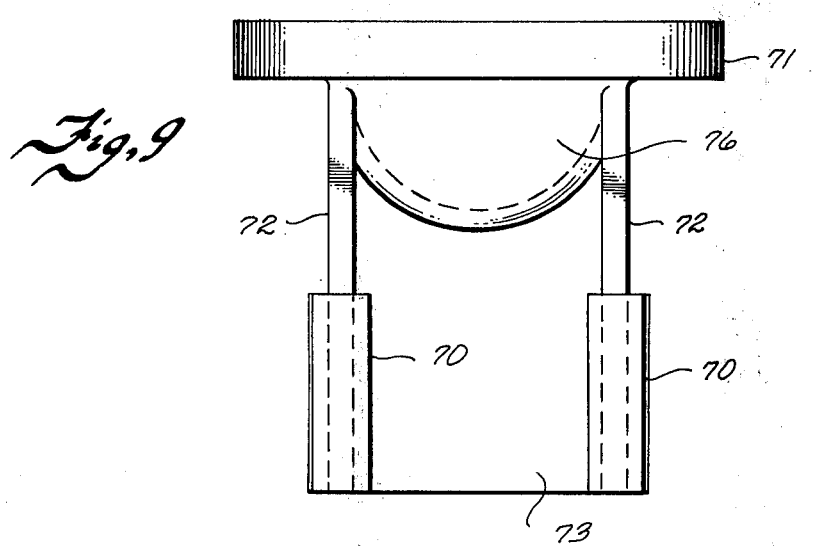
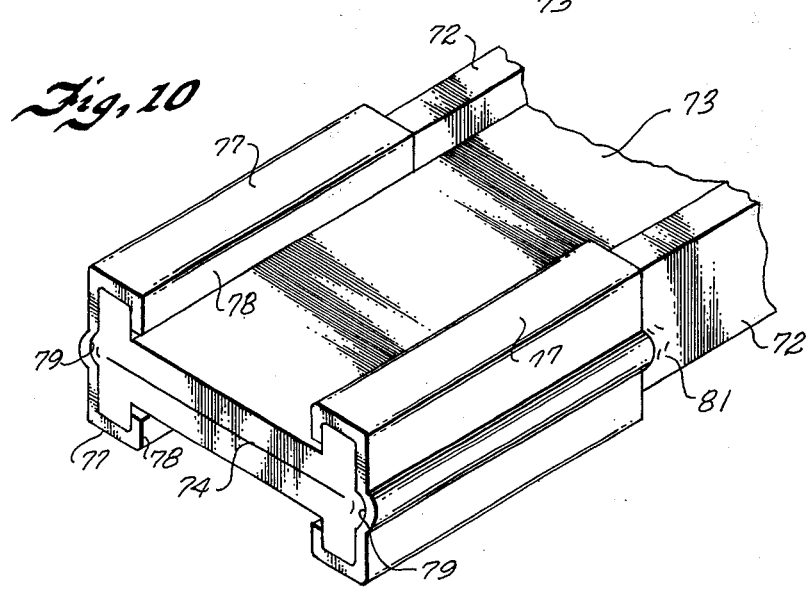

CHECK VALVE FOR URINE COLLECTION DEVICE

BACKGROUND

This is a continuation-in-part of copending application, Ser. No. 436,442 filed Jan. 25, 1974, now abandoned.

A large number of people have spinal cord injuries or other medical problems that cause bladder incontinence either on a temporary or permanent basis. In order for such persons to live a reasonably normal life, they are fitted with catheters for collecting the urine produced and conveying it to a temporary storage bag which is normally strapped to the person's leg during the day, or may be beside a bed during the night. Such urine collection arrangements have a variety of problems that range from annoyance and embarrassment to actual health hazard.

Incontinent persons may be fitted with either of two types of catheter, internal or external. An internal catheter has a tube through the urethra into the bladder and urine flows in small quantities as it is produced, through the catheter into the collection bag or other vessel. Except in situations where flow is deliberately impeded to force distention of the bladder, there is almost drop-wise flow through the catheter and into the bag.

Other persons are fitted with an external catheter which collects urine after it is excreted and directs it into the collection bag. In some patients there may be a small amount of urine flow on an intermittent basis, and in such cases the collection system handles only low amounts of flow as it does with an internal catheter. It is more usual, particularly in persons with spinal cord injury, that the musculature remains, but the person has no voluntary control of the bladder function. Urine may collect in the bladder for a substantial period, and an involuntary muscle spasm may initiate emptying. In such a situation there is a relatively rapid flow of urine from the catheter into the collection bag.

A significant problem with urine collection bags is back flow of urine therefrom. This may simply cause a spillage onto the clothing of the wearer which is an embarrassment and annoyance, and may damage clothing. More importantly, particularly with persons having an internal catheter, back flow of urine from the collection bag can carry microorganisms into the urinary tract, which can cause severe bladder or kidney infections. Such urinary tract infections are a continual hazard for persons using catheters on a permanent basis.

A variety of check valves have been devised for placement between the catheter and the urine collection bag. It is the purpose of these check valves to permit the urine to flow into the bag, but prevent back flow. All such prior valves have had significant shortcomings.

Urine is not a simple liquid, but is sometimes accompanied by tiny stones or other precipitated materials. Further, as the urine changes external to the body, there is a phenomenon known as granulation which involves a further precipitation of solid materials. This granulation can quickly degrade the performance of a check valve, and most particularly, lead to back leakage. Check valves with narrow seals are particularly subject to damage by granulation, since relatively small deposits can cause tiny openings that lead to back flow of stale urine and spread of infection.

A urine check valve must not only be free of back leakage, but must have an extremely low resistance to forward flow so that no more than a few drops of urine are sufficient for opening the valve and flowing therethrough. Sensitivity in check valves requires that there be very small force normally tending to close the valve. The desired sensitivity may be obtained by having a very narrow sealing line, but this is a problem due to granulation. If the valve has any substantial resistance to the flow of urine, pressure may be unintentionally increased in a bladder having an internal catheter so that urine flows around the exterior of the catheter and soils the person's clothing. Preferably, the check valve should drain to substantial dryness at all times.

The check valve should not only be sensitive to accommodate drop-wise flow, but for optimum scope of utilization, should also accommodate the full rate of flow during evacuation of a relatively full bladder. If the check valve will not accommodate the full flow of urine during the evacuation of a full bladder, spillage of the excess flow can scarcely be avoided.

One type of check valve that has been used in urine collection devices employs a thin-walled flat plastic or rubber tube that extends into the urine collection bag. Urine entering the upstream end of the tube takes very little force to flow therethrough. If such a tube is made by folding flat plastic materials or molding it in a flat shape, there is ordinarily a tiny passage along the lateral edges that may permit back flow of urine. Another significant problem with such a check valve is interference by the wearer's clothing. His clothing may actually bear on the flat tube in such a way that flow is inhibited and leakage may occur because the valve is effectively held closed. Conversely, the clothing may twist the tube in such a way that a small passage is formed to permit back flow of urine.

Granulation in urine collection check valves can be removed by adequate cleaning. However, it is necessary that there be access of the cleaning liquid to all portions of the valve so that it is basically clean when put into reuse. Alternatively, it is desirable that the check valve be sufficiently inexpensive so that it can be periodically replaced before granulation becomes a problem. A suitable check valve should be readily manufactured with a degree of precision and repeatability that assures high reliability. The check valve should be sensitive so that small amounts of urine freely flow through the valve and little, if any, urine collects or remains on the upstream side of the valve. The valve should also handle the full flow possible from the bladder without significant resistance. The valve should be sufficiently positive in closing that there is substantially no possibility of back flow of urine therethrough. The wearer's clothing should not interfere with operation of the valve.

SUMMARY OF THE INVENTION

There is, therefore, provided in practice of this invention according to a presently preferred embodiment a check valve for a urine collection system with a rigid body encasing an elastomeric sealing member. The sealing member has a pair of flat, parallel, normally spaced apart sealing leaves integrally joined together at their lateral edges for defining a flat tube with a flat passage between the leaves. Means are provided for pressing on the lateral edges of the leaves for forcing the edges of the passage closed. In a preferred arrangement the edges are enlarged and engaged by the body for holding the edges of the passage closed.

DRAWINGS

These and other features and advantages of the present invention will be appreciated as the same become better understood by reference to the following detailed description of a presently preferred embodiment when considered in connection with the accompanying drawings wherein:

FIG. 1 illustrates in longitudinal cross-section a urine check valve constructed according to principles of this invention;

FIG. 2 is a transverse cross-section through the valve of FIG. 1;

FIG. 3 is a perspective view of the sealing member of the check valve;

FIG. 4 is a fragmentary view illustrating part of another embodiment of sealing member;

FIG. 5 is a fragmentary view illustrating part of still another embodiment of sealing member;

FIG. 6 is a fragmentary view illustrating part of another embodiment of sealing member;

FIG. 7 is a fragmentary view illustrating another means for assuring closure of the check valve;

FIGS. 8 and 9 are side views of another embodiment of sealing member; and

FIG. 10 is a perspective view of one end of the sealing member with edge clips in place.

DESCRIPTION

In the embodiment of check valve illustrated in FIG. 1, there is a rigid upper body portion 11 having an elongated cylindrical neck 12 which can be inserted into the tube of a conventional catheter or otherwise connected to the catheter. The upper body has an axial bore 13 into which urine flows during use of the check valve. The lower portion of the upper body 11 has a male thread 14 engageable with the female thread 16 of a rigid lower body portion 17. The upper body has a central conical extension 18 which assures centering of a low friction plastic washer 19.

The lower body portion 17 has an inwardly directed flange 21 between the threads 16 and an open bottomed bore 22. The exterior of the lower body portion is cylindrical for receiving a urine collection bag (not shown). Ordinarily, such a bag is an elastomeric material that fits around the exterior of the lower body portion and is tightly held in place by an elastic strap.

It will be apparent that other arrangements on the exteriors of the upper and lower body portions can be provided for connecting the check valve into the flow stream between a catheter and a urine collection bag. Thus, for example, a relatively small size check valve can have its upper body portion fixed to an internal catheter with the lower body portion being connectable to tubing leading to any desired collection device. In such an arrangement a second check valve of similar construction may be added in series with the one more permanently connected to the catheter to prevent bag spillage. Such an arrangement gives the option of changing the collection bag at times different from that of changing the catheter, and either or both check valves serve to inhibit the flow of urine.

The two rigid body portions 11 and 17 are preferably injection molded from nylon or other suitable plastic material that is sufficiently inexpensive that the valve can be discarded if desired, and is also sufficiently durable that it can withstand repeated cleanings if that is the preference of the user.

A sealing member 23 has a peripheral end flange 24 between the inwardly directed flange 21 in the lower body portion and the washer 19. The sealing member is made of an elastomeric material that is preferably quite soft and flexible and has the ability to accommodate appreciable elastic extension. Since this material is soft, and proper functioning of the valve depends on its geometry, the low friction washer is provided between the upper body portion and the flange. This assures that when the threads between the two body portions ar tightened, there is good sealing of the elastomeric flange without appreciable twist being applied thereto which would tend to distort the soft rubber. Preferably, the elastomeric sealing member is a silicone rubber or other rubber-like material stable in the presence of urine and wettable thereby. Wetting of the sealing member is of importance in assuring that the last drops of urine are passed through the valve.

The sealing member has a pair of flat parallel leaves 26, which in a typical embodiment are only about 0.03 inch thick, so that they are quite flexible. The lateral edges of the leaves are joined together by integral webs 27 that extend along the length of the leaves. A flat, narrow passage 28 is provided between the leaves so that when the sealing member is separate from the rigid body, the passage is normally open. Thus, in effect, the two leaves 26 and connecting webs 27 form a flat tube having a relatively narrow flat passage 28 therethrough.

The reason the passage is left open is to permit ready manufacture of the sealing member. The parallel flat leaves 26 are relatively long, typically about 9/32 inch, and it is virtually necessary to form the passage during injection molding of the sealing member. The alternative is to cut a slit where the passage is desired after the sealing member has been molded. With the relatively long passage required for reliable sealing in presence of granulation, it is quite impractical to make such a deep cut in the rubber. Because of this impracticality, the alternative is to mold the passage at the time of molding the sealing member. This requires a blade of finite thickness in the mold and preferably such a blade is about 0.015 inch thick in order to assure its steady position and freedom from breakage in production molding equipment. Thus, when the sealing member is made, the flat leaves are normally spaced apart about 0.015 inch. It should be noted that the edges of the blade forming the passage are somewhat feathered and rounded off so that the edges of the passage taper slightly and have no sharp angles leading to excessive stress concentrations. If one were to cut a slit after molding, the lateral edges remain quite sharp and tearing of the delicate soft rubber can easily occur. A lack of integral web between the leaves can lead to leakage and makes assembly of the valve most difficult.

The flat leaves 26 are joined to the peripheral flange 24 by diverging flat sheets 29 integral with both the leaves and flange. This forms a wedge-shaped opening on the upstream end of the sealing member which effectively acts as a funnel for drops of urine reaching the check valve.

The lower bore 22 of the lower body 17 has T-shaped slots 31 extending longitudinally at either side. Each of the slots receives a pair of rectangular edge flanges 32 on each side of the respective web 27 on the sealing member. Thus, the lateral edges of the sealing member adjacent the leaves 26 have a generally T-shaped cross-section. The edge flanges 32 extend towards the center of the sealing member beyond the edges of the passage 28. The width of the T-slot 31 in the lower body is 0.015 inch narrower than the distance between the two flanges 32 on the sealing member. That is, the walls of the T-slot are spaced apart no more than the thickness of the elastomeric portion of the sealing member within the slot. Thus, when the sealing member is inserted, the walls of the slot press against the extending flanges 32 and force the edges of the passage 28 through the sealing member to be closed. This gives assurance that there is no small leakage path at the edges of the passage.

Since the leaves 26 of the sealing member are quite soft and flexible the pressing of their lateral edges together causes the passage 28 to be closed along its length. When urine flows through the check valve the center portions of the leaves 26 are spread apart and a portion of the spreading is obtained because of the elasticity of the rubber. Additional spreading can be accommodated by provision of a small amount of lateral clearance in the slot 31 for the flanges 32, permitting the lateral edges of the leaves to move inwardly or outwardly. The T-slots retain the lateral edges of the leaves so that heavy urine flow will not pull one or both of the edges out of the slot. This assures that the valve closes again when flow ceases.

It will be noted that the very soft nature of the elastomer and the low friction contact between the nylon body and the insert permits the valve to open with great sensitivity, yet reliably close when no fluid flows. If desired, a small amount of lubricant can be provided on the flanges 32 before insertion in the body both to ease insertion and to ease the lateral displacement.

To install the sealing insert in the body, the small insert is pressed into the lower body 17 so that the flanges 32 fit into the T-slots 31 on either side. This automatically closes the normally open passage 28 through the sealing member. The washer 19 is then dropped in place and the upper body portion 12 threaded in, finger tight, to make a seal. A quick look at the lower end of the valve assures that there has been no distortion of the rubber sealing insert which would cause back leakage.

After a period of usage, the valve can be disassembled and the insert discarded since it is quite inexpensive. Alternatively, a cleaning liquid can be passed through the check valve or a small brush can be used for cleaning the inside of the rubber sealing member and the entire check valve can be re-used.

FIG. 4 illustrates in fragmentary view an alternative edge structure for the leaves of the sealing member. In this arrangement there are a pair of flat, parallel, normally spaced apart, sealing leaves 36 having a connecting web 37 between their lateral edges so as to leave a normally open passage 38 therebetween. A pair of flanges 39 extend along the lateral edge on either side of the web 37 for fitting into the T-slots of a rigid mounting body for the soft rubber sealing member. The flanges 39 have a somewhat curved shape so as to be relatively further apart in that portion overlapping the passage 38 than nearer the web 37. This assures that the edges of the passage are closed when the member is inserted in the body. This shape further minimizes the force exerted between the flanges and body so that lateral displacement is easier. It might be noted that curved shape of the flanges fitted into a rectangular T-slot causes a slight bending at the lateral edges tending to pull on the leaves 36, thereby further assuring closure of the valve.

FIG. 5 illustrates in fragmentary perspective view another embodiment of soft elastomeric sealing member similar to that hereinabove described and illustrated. As illustrated in this embodiment the sealing member has a pair of flat parallel leaves 46 spaced apart by a flat passage 48. The leaves are integral with a web 47 along the lateral edges and rectangular flanges 49 extend along the length of the sealing member on either side of the respective web 47. To this extent the edge structure of the sealing insert is similar to that hereinabove described and illustrated in FIGS. 1–3. The embodiment of FIG. 5 has a groove 50 in one of the leaves 46, running along the lateral edge adjacent the flange 47. This reduces the thickness of that leaf, hence making it more flexible in this region and better able to deflect for opening the check valve. Such "weakening" can be provided in either or both edges of either or both leaves.

FIG. 6 illustrates in fragmentary perspective view a different embodiment of elastomeric sealing member for a urine check valve. As illustrated in this embodiment, the sealing insert has a pair of flat parallel leaves 56 joined together by webs 57 extending along the lateral edges. A flat, normally open passage 58 is provided between the leaves 56. When such an insert is employed, the slot (not shown) in the body in which it is mounted need not have a T-shape, but need only have a width corresponding to the combined thickness of the two leaves 56. The slots then press the edges of the two leaves together so that the passage 58 is forced closed. In other respects the body and insert are similar to that hereinabove described and illustrated.

It will be noted that in an embodiment as illustrated in FIG. 6, the lateral edges of the sealing member could come out of the slots in the body. The T-shaped slot and flanges hereinabove described and illustrated prevent this from occurring. It does not appear that absence of flanges along the lateral edges of the leaves is a great detriment if care is used in installing the sealing member in the rigid body. The flanges do add some stiffness along the edges of the insert and make assembly in the body somewhat easier.

FIG. 7 illustrates another embodiment of sealing member constructed according to principles of this invention. As illustrated in this embodiment, the sealing member has a pair of flat, parallel, normally spaced apart leaves 66 interconnected by an integral web 67 along each lateral edge. A narrow, flat, normally open passage 68 is provided between the two leaves to permit fluid flow. In this embodiment, a small metal or plastic clip 69 having a U-shaped cross section is clamped along each side edge of the leaves overlapping the web 67 and a portion of the passage 68. The clip presses on the edges of the leaves and forces the passage 68 into closed position as illustrated in FIG. 7. The clip can be employed in lieu of the slots extending along the length of the rigid body in which the sealing member is mounted. This leaves the lateral edges of the leaves completely free from interference with the body and assures easy opening of the check valve and reliable closing.

FIGS. 8 and 9 are two orthogonal side views of a presently preferred embodiment of a sealing member for a check valve as provided in practice of this invention. In FIG. 8 the sealing member is shown by itself and in FIG. 9 it has a pair of edge clips 70 in place. The lower end of the sealing member and edge clips are also illustrated in a fragmentary perspective in FIG. 10. In most respects this sealing member is substantially similar to that hereinabove described and illustrated in the perspective view of FIG. 3.

The sealing member has a circular end flange 71 at what is normally its upper end when in place in the check valve. A pair of edge flanges 72 extend down each side of the sealing member from the end flange 71. The edge flanges 72 are interconnected by a pair of leaves 73 having a normally open passage 74 therebetween. A hollow spherical membrane 76 interconnects the upper ends of the leaves to the end flange 71 and performs somewhat like a funnel in use of the valve. As above described, the sealing member is molded as a single piece of soft elastomer. Preferably the leaves in the embodiment of FIG. 8 are slightly narrower than those in the embodiment hereinabove described so as to freely fit within a rigid valve body having an outside diameter the same as that in FIGS. 1 and 2. The rigid valve body (not shown) is substantially the same as the one in FIGS. 1 and 2, except that it has a cylindrical bore in the lower section rather than the provision for slots to receive the edge flanges 72.

As best seen in the perspective view of FIG. 10, the clips 70 are generally U-shaped and have a pair of parallel legs or sides 77 that fit over the edge flanges 72 of the sealing member. Each of these sides 77 has an inwardly directed lip 78 that retains the clip in place on the sealing member. The sides 77 of the U-shaped clip are spaced apart no more than the thickness of the elastomeric material therebetween; that is, they are no further apart than the total width of the flange 72 less the thickness of the normally open passage 74. Thus, when in place on the sealing member, the edges of the normally open passage are forced closed. For example, when the width of an edge flange 72 is about 0.155 inch and the normally open slot has an opening of about 0.015 inch, the sides 77 of the clip are slightly less than 0.140 inch apart so that the slot is forced closed. Thus, when the clips are in place as in FIG. 10 the slot 74 is closed and when the clips are absent, the slot stands open much in the manner illustrated in FIG. 3.

It will be noted that the clips overlap the web between the leaves and the edges of the normally open passage, thereby causing the full width of the passage to be closed when there is no liquid pressure acting on the leaves. Since the clips are free from the body of the check valve, there is no appreciable resistance to opening of the passage by a very small amount of liquid between the leaves. The two clips merely move a slight distance towards each other to accommodate a very small amount of opening. If the flow through the check valve is appreciable so that the leaves are forced apart an appreciable distance the clips are free to move a larger amount to accommodate this increased flow.

Each of the clips has a relief groove 79 running along its length midway between the sides 77. This groove accommodates a slight bulge 81 in the soft elastomer of the edge flanges 72 when the slot is squeezed closed. This groove can also accommodate any slight molding flash that may remain in this region. It will be apparent that relief for the bulge and flash can be provided by a pair of faces not quite at right angles to the sides faces 77 without significantly affecting the support for the edge flanges. Such a construction can be considered equivalent to the more pronounced relief groove illustrated in FIG. 10.

In a urine check valve it is of considerable importance that the valve drain nearly completely dry and that it open with only a drop or two of liquid. It has been found that resistance to opening of the check valve is primarily due to the resistance at the upper ends of the leaves, that is, adjacent the funnel-like portion between the leaves and the end flange. The leaves, as best seen in FIG. 8, are made quite thin near the upper end adjacent the flange and somewhat thicker at the more remote end where the liquid exits. Typically, for example, the leaves are only about 0.015 inch thick near the spherical membrane 76 and gradually taper to a thickness of about 0.030 inch at the free end remote from the funnel-like portion. The very thin leaves are readily opened by a tiny amount of liquid and once opening has commenced liquid will flow through the check valve in its forward direction even though the leaves are of somewhat thicker cross section. A somewhat greater thickness is desirable at the free end of the leaves to give the elastomeric sealing member greater strength and rigidity.

It will also be noted that the clips extend only part of the way along the length of the flanges on the leaves. They stop short of the region where the leaves first open and therefore have no appreciable inhibition to opening of the check valve.

It is found in testing check valves as hereinabove described and illustrated that when first put into service only a few drops of liquid are required to develop sufficient head to commence the flow of liquid through the valve. Once this has occurred and the surfaces are wetted by the liquid, the valve essentially drains completely dry without any liquid standing on the upstream side of the valve. Only the liquid wetting the valve surfaces appears to remain in the valve. Even the small starting amount can be minimized by prewetting the sealing member before assembling the valve to the catheter. After the valve surfaces are wetted, only a drop or two of urine ever remains on the upstream side since the valve readily opens to permit its passage.

Conversely, the valve can be inverted and appreciable head applied, or the contents on the downstream side of the valve can be shaken, and no back flow of urine occurs.

Thus, the check valve described and illustrated herein is extremely sensitive to very small quantities of liquid on the upstream side and is completely resistant to back flow of liquid from the downstream side. The sealing member is completely encased in a rigid housing so that functioning of the valve is not hindered by the wearer's clothing. For these reasons the check valve hereinabove described and illustrated is particularly suitable for use in a urine collection device.

Although limited embodiments of urine check valve constructed by principles of this invention have been described and illustrated herein, many modifications and variations will be apparent to one skilled in the art. Thus, for example, in lieu of using a T-shaped pair of flanges along each lateral edge of the sealing member, the edges of the leaves can be essentially L-shaped with a single flange on each lateral edge of the leaves. A single flange is sufficient for preventing the leaves from being pulled out of the slot in the body or out of the edge clip and the lateral edges can be slightly less stiff. If both L-shaped slots face clockwise (or counterclockwise) in the body the sealing insert can also be symmetrical and placed in either of the two possible orientations in the body. The edge clips can, of course, be fitted on either L-shaped edge flange since they can be freely placed on from either end. Many other modifications and variations will be apparent to one skilled in the art. It is therefore to be understood that within the scope of the appended claims the invention may be practiced otherwise than is specifically described.

What is claimed is:

1. A liquid check valve having no back leakage and capable of draining substantially dry in the forward direction comprising:
   a rigid body having a passage therethrough;
   an elastomeric sealing member mounted within the body, said sealing comprising:
   a pair of flat, parallel, normally spaced apart, sealing leaves;
   a web among each lateral edge of the sealing leaves and integral therewith for joining the adjacent edges of the leaves together, said leaves and webs collectively defining a flat tube having a flat, normally open, passage therethrough; and
   a peripheral end flange integral with the leaves for mounting the sealing member in the body; and
   means for pressing on the lateral edges of the leaves for forcing the lateral edges of the flat passage closed, comprising spaced apart wall portions extending longitudinally in the rigid body for receiving the lateral edges of the sealing leaves, said wall portions being spaced apart no more than the thickness of the elastomer portion of the sealing member therebetween.

2. A liquid check valve having no back leakage and capable of draining substantially dry in the forward direction comprising:
   a rigid body having a passage therethrough;
   an elastomeric sealing member mounted within the body, said sealing member comprising:
   a pair of flat, parallel, normally spaced apart, sealing leaves;
   a web among each lateral edge of the sealing leaves and integral therewith for joining the adjacent edges of the leaves together, said leaves and web collectively defining a flat tube having a flat, normally open, passage therethrough; and
   a peripheral end flange integral with the leaves for mounting the sealing member in the body;
   a longitudinally extending lateral flange portion adjacent each web; and
   means for pressing on the lateral edges of the leaves for forcing the lateral edges of the flat passage closed, comprising a slot in the body for receiving the flanged portion and having a width no more than the thickness of the elastomeric portion of the sealing member received within the slot.

3. A liquid check valve as defined in claim 2 wherein the flanged portion comprises a pair of flanges defining a T-shaped lateral edge along each lateral edge of the leaves, and wherein the longitudinal slot in the body has a T-shaped cross-section.

4. A liquid check valve as defined in claim 2 wherein the sealing member further comprises a longitudinally extending groove in a leaf adjacent the flange portion for reducing cross section of the respective leaf and reducing resistance to deflection.

5. A liquid check valve having no back leakage and capable of draining substantially dry in the forward direction comprising:
   a rigid body having a passage therethrough;
   an elastomeric sealing member mounted within the body, said sealing member comprising:
   a peripheral end flange;
   a pair of edge flanges extending downward from the end flange;
   a pair of flat, parallel, normally spaced apart sealing leaves integral with the end flange wherein each leaf is relatively thinner nearer the peripheral end flange and relatively thicker remote from the end flange;
   a hollow spherical membrane interconnecting the ends of the leaves nearer the end flange to the end flange; and
   means for pressing on the lateral edges of the leaves for forcing the lateral edges of the flat passage closed, comprising a slot in the body for receiving the flanged portion and having a width no more than the thickness of the elastomeric portion of the sealing member received within the slot.

6. A liquid check valve having no back leakage and capable of draining substantially dry in the forward direction comprising:
   a rigid body having therethrough;
   an elastomeric sealing member mounted within the body, said sealing member comprising:
   a pair of flat, parallel, normally spaced apart, sealing leaves;
   a web among each lateral edge of the sealing leaves and integral therewith for joining the adjacent edges of the leaves together, said leaves and web collectively defining a flat tube having a flat, normally open, passage therethrough; and
   a peripheral end flange integral with the leaves for mounting the sealing member in the body; and
   a generally U-shaped rigid clip along each lateral edge of the leaves for forcing the edges of the leaves together, and hence closing the normally open passage, said clips being separate from the rigid body and from each other.

7. A liquid check valve as defined in claim 6 further comprising a T-shaped flange portion along each lateral edge of the leaves overlapping the web and an edge portion of the normally open passage, each U-shaped clip compressing the T-shaped flange portion and closing an edge of the normally open passage.

8. A liquid check valve as defined in claim 7 wherein the passage has tapered or feathered lateral edges without any sharp corners.

9. A liquid check valve as defined in claim 6 wherein each clip includes a relief groove adjacent the web for accommodating bulging of the sealing member upon compression of the flange portion.

10. A liquid check valve as defined in claim 6 wherein each leaf is relatively thinner at the end nearer the end flange and relatively thicker at the end remote therefrom.

11. In an elastomeric sealing member for a urine check valve comprising a pair of flat, parallel, normally spaced apart, sealing leaves; a web along each lateral edge of the sealing leaves and integral therewith for joining the adjacent edges of the leaves together, said leaves and webs collectively defining a flat tube having a flat passage therethrough; a peripheral flange at one end for mounting the sealing member; and a funnel-like section integral with the flange and leaves for forming a transition therebetween, the improvement wherein the flat passage between the leaves is normally open with the leaves spaced apart a small distance, and wherein each leaf is relatively thinner adjacent the funnel-like section and relatively thicker at the end remote therefrom, and the faces of the leaves defining the flat passage are uniformly spaced apart through the length of the passage.

12. In an elastomeric sealing member for a urine check valve comprising a pair of flat, parallel, normally spaced apart, sealing leaves; a web along each lateral edge of the sealing leaves and integral therewith for joining the adjacent edges of the leaves together, said leaves and webs collectively defining a flat tube having a flat passage therethrough; a peripheral flange at one end for mounting the sealing member; and a funnel-like section integral with the flange, and leaves for forming a transition therebetween, the improvement wherein the flat passage between the leaves is normally open with the leaves spaced apart a small distance, and there is a generally U-shaped rigid clip along each edge of the leaves, the sides of each U-shaped clip being spaced apart no more than the thickness of the elastomeric material therebetween for forcing the edges of the normally open passage closed.

13. In a combination as defined in claim 12 the further improvement wherein each clip further comprises a relief groove adjacent the web for accommodating bulging of the sealing member upon closing of the edges of the normally open passage.

14. In an elastomeric sealing member for a urine check valve comprising a pair of flat, normally spaced apart, sealing leaves; a web along each lateral edge of the sealing leaves and integral therewith for joining the adjacent edges of the leaves together, said leaves and webs collectively defining a flat tube having a flat passage therethrough; a peripheral flange at one end for mounting the sealing member; and a funnel-like section integral with the flange and leaves for forming a transition therebetween, the improvement wherein the flat passage between the leaves is normally open with the leaves spaced apart a small distance and wherein the leaves are substantially continuously tapered in thickness with the thinner part adjacent the funnel-like section.

\* \* \* \* \*

UNITED STATES PATENT AND TRADEMARK OFFICE
CERTIFICATE OF CORRECTION

PATENT NO. : 3,967,645
DATED : July 6, 1976
INVENTOR(S) : Roy Gregory

It is certified that error appears in the above—identified patent and that said Letters Patent are hereby corrected as shown below:

Column 4, line 12, "ar" should be -- are --.

Column 10, line 24, -- a passage -- should be inserted after "having" and before "therethrough".

Signed and Sealed this

Seventh Day of September 1976

[SEAL]

Attest:

RUTH C. MASON
*Attesting Officer*

C. MARSHALL DANN
*Commissioner of Patents and Trademarks*